United States Patent [19]

Mäder et al.

[11] Patent Number: 4,802,480

[45] Date of Patent: Feb. 7, 1989

[54] METHOD FOR TREATING PORTIONS OF THE HUMAN BODY

[75] Inventors: Karl Mäder, Pfäffikon; Guido Schönenberger, Reinach; Carlo A. Buzzi, Zürich, all of Switzerland

[73] Assignee: I D C - Chemie AG, Freienbach, Switzerland

[21] Appl. No.: 87,321

[22] Filed: Aug. 20, 1987

Related U.S. Application Data

[63] Continuation of Ser. No. 856,990, Apr. 29, 1986, Pat. No. 4,711,375.

[30] Foreign Application Priority Data

May 17, 1985 [CH] Switzerland .......................... 2123/85

[51] Int. Cl.$^4$ ................................................ A61F 7/00
[52] U.S. Cl. .................................... 128/400; 604/291; 424/DIG. 13
[58] Field of Search .................. 604/49, 112, 113, 289, 604/290, 291; 424/DIG. 13; 128/399, 400, 24.1, 200.19, 303.1, 156, 132; 239/305; 62/64, 74

[56] References Cited

FOREIGN PATENT DOCUMENTS

84/04883 12/1984 PCT Int'l Appl. .................. 604/291
628905 9/1978 U.S.S.R. ............................... 604/291

Primary Examiner—Richard C. Pinkham
Assistant Examiner—Mark S. Graham
Attorney, Agent, or Firm—Bernard, Rothwell & Brown

[57] ABSTRACT

A method of treating burns and scald wounds on the human body by rapid cooling which includes spraying liquid from a hand-held container and directing the liquid to the portion of the human body to be treated to form a film of liquid and then spraying and directing onto the film of liquid from a second hand-held container a refrigerant at a temperature low enough and a flow rate high enough to freeze a substantial portion of the film of liquid so that the human body is rapidly cooled by the heat absorbed from the frozen film. An apparatus accomplishing the method includes a portable hand-holdable support with two containers, one having sprayable liquid and the other having a refrigerant.

3 Claims, 2 Drawing Sheets

METHOD FOR TREATING PORTIONS OF THE HUMAN BODY

CROSS REFERENCE TO RELATED APPLICATIONS

This is a continuation of commonly assigned, copending U.S. application Ser. No. 856,990, filed Apr. 29, 1986 now U.S. Pat. No. 4,711,375.

FIELD OF THE INVENTION

The invention relates to apparatus and methods for treating portions of the human body, in particular burn or scald wounds and other localized body conditions through rapid cooling to provide beneficial results.

BACKGROUND OF INVENTION

For many years, medical research has been conducted on the treatment of burn and scald wounds on the human body. In the case of severe burn wounds, it has been found that even after the patient's condition has stabilized, serious infections often occur, sometimes with lethal consequences. In such cases, severely burned patients who survived the post-traumatic shock often developed what is called late burn disease resulting in death in a late phase with the apparent clinical picture of a local and generalized infection, i.e. sepsis. For many years, clinicians postulated the occurrence of one or more toxic substances produced by thermal energy in the skin as the basic cause of the late mortality.

More recent biochemical and biological investigations conducted by the present inventors and others have isolated and characterized a toxic lipid protein complex called "burn toxin" as the basic cause of late burn disease. In the course of research conducted by the present inventors in burn therapy, a number of instances were noted in which severely burned patients were found to have a better chance of survival if the burns were rapidly cooled immediately after even third degree burns had already developed. Several of these instances occurred when the victims were burned as a result of an accident on a boat and jumped into cold sea water immediately thereafter. In other instances, reports came from burn centers that cooling with tap water prevented significantly the development of hypertrophic scars of healing burn wounds, thereby avoiding the need for long lasting, expensive plastic and reconstructive surgery in the reconvalescence phase.

These phenomena are of importance not only with regard to the survival of the patients involved but also with respect to the shortening and easing or even elimination of complications in the reconvalescence phase and finally realizing better cosmetic results as well.

It has now been confirmed that these toxic substances or burn toxins formed by thermal decomposition of proteins weaken the immune defense so that the body is unable to resist the unavoidable invasion of bacteria through the wound area. It has been found that immediate and rapid cooling, i.e. within thirty to sixty seconds, after occurrence of the burn wound with cold water produces favorable results in several respects. In addition to immediately reducing the pain, the decomposition of proteins and the development of burn toxins is greatly reduced or even eliminated.

However, sources of cold water, ice or other cooling means are not always immediately available when a burn accident occurs. This is often the case in outdoor situations during work or in recreation time, in heavy traffic situations and often in certain household, office and school environments as well. In addition many people, in fact probably most people, are not aware of the enormous beneficial effects of immediate cooling of burn wounds and therefore adopt a large variety of so-called curative actions ranging from the application of flour, olive oil or butter or even so-called cooling leaves to the burn as well as other often traditional local "therapies". These measures are often more harmful than beneficial.

SUMMARY OF THE INVENTION

This invention comprises, in one embodiment thereof, a method for treating burns and similarly damaged areas of the human body, which method can be quickly and easily utilized through a self contained and hand portable apparatus which can be stored for relatively long periods of time in readily accessible locations where access to cooling media may not be conveniently available or even available at all. The apparatus for carrying out the method may, for example, be stored in a first aid kit or in a medicine cabinet, an automobile or other locations where medical supplies may customarily be kept. With the portable apparatus, the method of rapidly cooling the burn can be practiced quickly and effectively to greatly inhibit or even prevent significant development of burn toxins.

The apparatus of the invention comprises, in one embodiment thereof, a device having two containers, one of which contains a liquid, preferably sterile water or a mixture comprised substantially of sterile water and one or more other ingredients such as an antiseptic agent, and the other of which contains a refrigerant which, when expelled from the container, absorbs heat. The device includes hand or finger operated valves or pump means for separately expelling the liquid water or water solution and the refrigerant. The water is preferable expelled in a spray form and the refrigerant stored in a liquid form and expanded to its gaseous state upon release from the container, and thereby greatly reduced in temperature and capable of absorbing heat.

The method is practiced, utilizing this embodiment, by hand operating the valve or pump means to spray water from the hand held device and directing the spray on to the burn wound to form thereon and preferably over the entire surface thereof a film of water or water solution. Thereafter, valve means are manually operated to expel the refrigerant from the hand held device. The refrigerant is directed onto the surface of the liquid for a sufficient time period to cause rapid cooling thereof and to cause the liquid, or at least substantial portions thereof, to undergo a phase change to the solid state or ice form. The frozen liquid in direct contact with the burned tissue absorbs heat rapidly and in large quantities from the burned tissue, thereby greatly inhibiting or substantially preventing formation of burn toxins. The method may be repeated periodically at intervals dependent upon the severity of the burn.

The method of the invention may also be used to treat portions of the human body where localized reduction in metabolic processes is desired such as, for example, local infections, distortions due to hemorrhagic swelling, muscle and other localized pains or aches where periodic cooling is known to be beneficial.

DETAILED DESCRIPTION OF THE INVENTION

Figure 1:
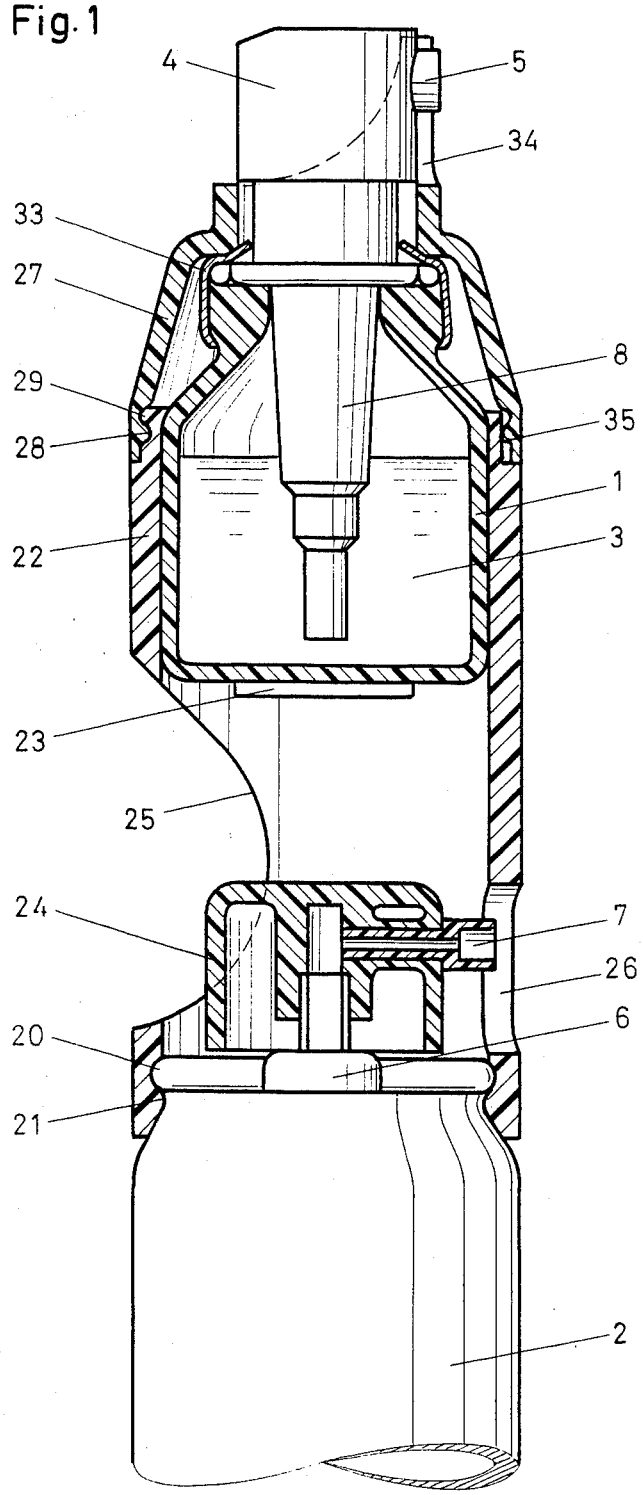
FIG. 1 is a side view, taken partly in cross section, of the essential portions of a device embodying the present invention.

In the embodiment shown in FIG. 1, the device comprises two containers 1 and 2 positioned coaxially one above the other. Container 1 preferably holds sterile water 3 which may include other ingredients as well such as, for example, an antiseptic or medicinal ingredient. Container 1 is considerably smaller than container 2 which holds a refrigerant such as a fluorohydrocarbon or $CCl_2$ typically stored in the container 2 in liquid form.

A housing 22 is snapped onto a flanged edge 20 of container 2 by means of a ring-shaped projection 21. The housing 22 has a cylindrical hole and an axial stop 23 to receive container 1. A button 24 is provided for operation of a valve 6 of container 2. To allow finger operation of the button 24, housing 22 has an access opening 25. Diametrically opposite the access opening 25, housing 22 has an elongated hole 26 into which a spray nozzle 7 of valve 6 projects.

Container 1 is held in housing 22 by a snap-on guide cap 27. The cap 27 engages a projection 29 of housing 22 with a ring-shaped projection 28. A pump 8 that projects to the base of container 1 is mounted on container 1 by means of a flanged crown 33 so that it is airtight. Spring loaded operating button 4 of pump 8 has a spray nozzle 5 which is guided in an axial slit 34 of guide cap 27. Guide cap 27 has a projection 35 which engages an axial groove of the housing 22 so that slit 34 is flush with elongated hole 26 and thus the two spray nozzles 5 and 7 are aligned in parallel.

The container 1 holds a liquid 3 which is preferably sterile water which may optionally be mixed with small quantities of additional ingredients such as an antiseptic or other medicinal ingredients. The liquid 3 may also be a liquid other than water or a water mixture as long as it is capable of being frozen under the conditions to be described and preferably has a relatively high specific heat. The formula of the liquid 3 should be selected, however, such that it is harmless if it enters body cavities such as the eyes or the mouth. For the embodiment shown, however, sterile water or a sterile water mixture is preferred. For purposes of the description which follows, liquid 3 will be referred to as sterile water, although it be understood that other liquids may be used.

The sterile water 3 remains sterile in container 1 for a long period of time because of the airtight seal of container 1. It therefore has a long shelf life for storage purposes. Pump 8 is manually operable by means of repeated depression of the button 4 and assures safe and reliable operation of the device even after years of storage. Instead of pump 8, however, bubble storage would also be possible, where the water would be separated from a propellant gas by a membrane.

Stored in container 2 is a refrigerant such as $CCl_2F_2$. Fluorocarbons which are neither flammable nor toxic and do not cause any irritation of the mucosa are especially suitable refrigerants. Such compounds are known as safety refrigerants. Especially suitable is dichlorodifluoromethane ($CCl_2F_2$) and/or chlorodifluoromethane ($CHClF_2$) with boiling points of $-29.8°$ C. and $-40.8°$ C. at 1 bar. To adjust the vapor pressure and thus also the refrigeration effect, $CCl_2F_2$ and/or $CHClF_2$ may also be mixed with $CCl_3F$, $CClF_2—CCl_2F$ or with $CClF_2—CClF_2$.

Figure 2:
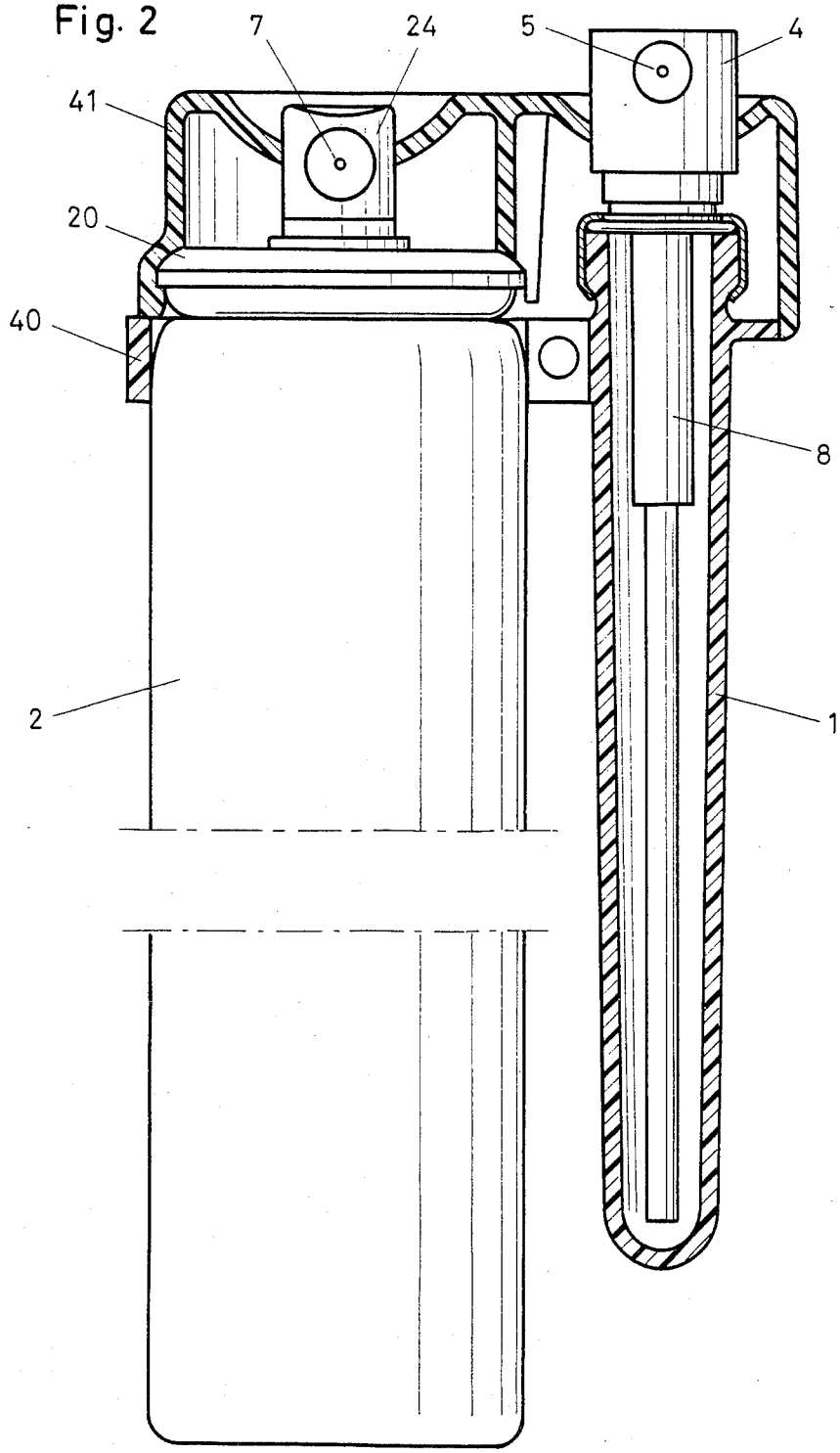
FIG. 2 is a full side view, also taken partly in cross section, of an alternative device design also embodying the present invention.

In the embodiment shown in FIG. 2, the two containers 1 and 2 are placed side by side. Container 1 is supported in and is a part of a housing 40 which is placed on container 2 and is secured by a guide cap 41 snapped on a flanged edge 20 of container 2. The guide cap 41 has a guide slit for guiding the two spray nozzles 5 and 7, like the guide slit 34 in the embodiment of FIG. 1. As in the case of the embodiment of FIG. 1, a liquid such as sterile water, a sterile water mixture or other liquid as discussed is stored in container 1 and sealed therein and a refrigerant is stored in container 2.

Other arrangements of the two containers 1 and 2 may be employed. The two containers may also be in the form of separate chambers in a single container structure as long as they function as separate containers.

In both embodiments as shown in FIGS. 1 and 2, the container 2 is substantially larger than container 1. This is because the storage volume for the amount of refrigerant required to freeze the volume of liquid 3 in container 1 is very much larger than the volume of liquid 3. Also a certain amount of the refrigerant will unavoidably be wasted in the spraying process and additional volume is required in container 2 to allow for waste.

OPERATION AND METHOD

The devices of the embodiments of FIGS. 1 and 2 are both operated in a similar manner to practice the method of the present invention.

In the case of the embodiment of FIG. 1, the device is held in the hand and one or more fingers used to repeatedly depress the button 4 to cause a spray of sterile water to be emitted from the spray nozzle 5. The sterile water spray is manually directed onto the burn wound and the device is moved about in the process until the area of the wound is covered with a film of liquid sterile water.

The finger is then moved through the access opening 25 to depress the button 24 and cause a stream of refrigerant to be emitted from the spray nozzle 7. The refrigerant typically expands from the liquid form as it is released and is emitted as a cold gas. The stream of refrigerant is manually directed from the nozzle 7 onto the sterile water film previously formed over the burn wound. The refrigerant stream is moved about and directed over the area of the liquid film to absorb heat therefrom until all or substantially all of the film over the wound has been converted to the frozen state.

As the frozen film is formed, it immediately kills the pain and prevents, counteracts and stops protein denaturation, i.e. destruction and disintegration of skin and tissue involved in the burn or scald area. The treatment can be repeated periodically by following the steps described until the burn area has calmed down enough to allow other measures to be taken.

Thus the burn wound is effectively cooled without damaging the tissue due to excessively low temperatures. The cooling effect lasts for a longer period of time due to the great cooling capacity of the ice. It is advisable to repeat the treatment after about 20 minutes, or in the case of severe burns, to repeat it several times at longer intervals. The treatment described here is a first aid measure and does not replace treatment by a physician, but it does assure subtantially greater prospects of success.

The sterile water solution formula is preferably designed so that entrance into the eyes, body cavities such as the mouth, or other open wounds is harmless. The initial spray application of the sterile water in liquid form has several other advantages. First it provides a cleaning or rinsing effect on the wound area. Secondly, it protects the wound area from direct exposure to the extreme cold of the refrigerant stream. In addition, application in liquid form allows penetration through most fabrics and allows fast application to the skin without the necessity for removal of clothing. Since the refrigerant is in a gaseous form as applied, it too will penetrate most clothing fabrics and allow freezing of the film directly on the skin.

A typical application using the above described method and using visual or patient reaction means to detect formation of the frozen film will result in a film temperature of about $-10°$ C. to $-15°$ C. so that the cooling effect is immediate and efficient as well as is the pain killing capacity. The frozen film can be applied over a large area in a a single application by moving the device back and forth as the application steps of the liquid film and the refrigerant are carried out.

In addition to reducing or preventing formation of burn toxins, the frozen layer also slows down the local metabolic process in the area of its application. The method and apparatus of the invention can therefore also be used to treat portions of the body where localized reduction of metabolism is desired such as in the case of local infections, swellings, muscle aches and other localized aches or pains where periodic cooling is known to be beneficial.

The apparatus of the present invention is lightweight, easily portable and is structured to be hand held in operation. It can be conveniently stored as a first aid item in about the same space as occupied by the typical aerosol can. The apparatus of the invention may, of course, take forms other than those illustrated and described, it being understood that the specificity of disclosure is made for full and clear description of the embodiments presented, and not by way of limitation. The apparatus may, for example, may be packaged as two separate containers having the characteristics of the liquid and refrigerant as described and including instructions for the practice of the method of this invention. Or the two containers may be separate cavities in a single structure as previously noted.

As mentioned above, the liquid to be frozen may be a liquid other than sterile water as long as its properties are matched to those of the refrigerant and are otherwise compatible with the practice of the method of the present invention.

It should thus be understood that various changes, modifications and adaptations may be made in the embodiments of the invention as shown and described herein without departing from the true scope and spirit of the invention, and that such changes, modifications and adaptations are intended to be comprehended within the scope and range of equivalents of the appended claims.

We claim:

1. A method of treating burn and scald wounds and localized disorders on portions of the human body by rapid cooling thereof comprising the steps of:
   (a) spraying a liquid from a first hand held container;
   (b) directing the sprayed liquid at the human body portion to be treated to form thereon a film of said liquid; and
   (c) spraying and directing onto said film of liquid from a second hand held container a refrigerant at a temperature low enough and at a flow rate high enough to freeze a substantial portion of said film of liquid, whereby said human body portion is rapidly cooled by heat absorbed by the frozen film, and wherein the steps of spraying a liquid from a first hand held container and of spraying a refrigerant from a second hand held container are performed with said first and second containers provided in a single hand held device.

2. The method of claim 1 in which said liquid is comprised substantially of sterile water.

3. The method of claim 1 in which said liquid is comprised substantially of stored sterile water and in which said refrigerant is a stored liquid under pressure in said second container and in which the low temperature of the refrigerant is achieved by evaporation.

* * * * *

UNITED STATES PATENT AND TRADEMARK OFFICE
CERTIFICATE OF CORRECTION

PATENT NO. : 4,802,480
DATED : FEBRUARY 7, 1989
INVENTOR(S) : KARL MADER, ET AL.

It is certified that error appears in the above-identified patent and that said Letters Patent is hereby corrected as shown below:

Front Page, [63], after "Continuation" insert -- In Part --.

Column 1, line 8, after "continuation" insert -- in part --.

Signed and Sealed this

Tenth Day of April, 1990

Attest:

HARRY F. MANBECK, JR.

*Attesting Officer*      *Commissioner of Patents and Trademarks*